United States Patent
Bretzler et al.

[11] Patent Number: 5,871,717
[45] Date of Patent: *Feb. 16, 1999

[54] ANTIPERSPIRANT CREAM COMPOSITIONS HAVING IMPROVED RHEOLOGY

[75] Inventors: Eric John Bretzler, deceased, late of Fisherville, Canada, by Erma Fern Bretzler, administratix; Christine Marie Putman, West Chester, Ohio; Ghebre Egziabher Tzeghai, Wyoming, Ohio; David Frederick Swaile, Cincinnati, Ohio

[73] Assignee: Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 738,631

[22] Filed: Oct. 29, 1996

Related U.S. Application Data

[63] Continuation-in-part of Ser. No. 557,637, Nov. 14, 1995, abandoned, and a continuation-in-part of Ser. No. 557,249, Nov. 14, 1995, abandoned.

[51] Int. Cl.$^6$ ............................. A61K 7/32; A61K 7/00
[52] U.S. Cl. ......................... 424/65; 424/400; 424/401
[58] Field of Search ................................ 424/65, 66, 67, 424/68, 400, 401

[56] References Cited

U.S. PATENT DOCUMENTS

| | | | |
|---|---|---|---|
| 4,126,679 | 11/1978 | Davy et al. | 424/66 |
| 4,526,780 | 7/1985 | Marschner et al. | 424/66 |
| 4,725,432 | 2/1988 | May | 424/66 |
| 4,749,569 | 6/1988 | Gianino et al. | 424/65 |
| 4,840,789 | 6/1989 | Orr et al. | 424/66 |

(List continued on next page.)

FOREIGN PATENT DOCUMENTS

| | | |
|---|---|---|
| 1125659 | 6/1982 | Canada . |
| 0 135 315 A2 | 3/1985 | European Pat. Off. . |
| 2018590 | 10/1979 | United Kingdom . |
| 92/19215 | 11/1992 | WIPO . |

OTHER PUBLICATIONS

German Patent Publication DE 4309372 A1 940929 (English Abstract) Derwent, Acc. No. 94–303652, Klier, Schneider, Traupe, Voss, Wolf, Roeckl, Siemanowski, Uhlig, "Deodorants".

Japan Patent Publication JP 52099236 A 770819 (English Abstract) Derwent Acc. No. 77–69889Y, Yoshida, Aoyagi, Nakano, "Antiperspirant".

(List continued on next page.)

*Primary Examiner*—Shelley A. Dodson
*Attorney, Agent, or Firm*—William J. Winter; Tara M. Rosnell; David L. Suter

[57] ABSTRACT

Disclosed are anhydrous antiperspirant cream compositions that are substantially free of polymeric or inorganic thickening, and have improved product stability and spreading performance. These compositions have a rheology profile characterized by select product hardness (from about 75 gram force to about 500 gram force), delta stress (from about 300 dyne/cm$^2$ to 8,000 dyne/cm$^2$) and static yield stress (at least about 1,000 dyne/cm$^2$) values. The new rheology profile is preferably applied to antiperspirant cream compositions comprising from about 0.1% to about 20% by weight of a crystalline gellant, from about 10% to about 80% by weight of an anhydrous liquid carrier for the crystalline gellant having a solubility parameter of from about 3 to about 13 and, from about 5% to about 35% by weight of a particulate antiperspirant active. Also disclosed are methods of using and making the compositions, and packaged compositions having a shear force delivery means for applying the composition to the axilla or other area of the skin. The disclosed compositions are especially effective at minimizing or eliminating solvent syneresis during packaging, storage, transport or during extrusion through a perforated mesh cap or other shear force delivery means.

47 Claims, 2 Drawing Sheets

U.S. PATENT DOCUMENTS

| | | | |
|---|---|---|---|
| 4,937,069 | 6/1990 | Shin | 424/66 |
| 4,944,937 | 7/1990 | McCall | 424/65 |
| 4,985,238 | 1/1991 | Tanner et al. | 424/66 |
| 4,996,239 | 2/1991 | Matravers | 514/873 |
| 5,000,356 | 3/1991 | Johnson et al. | 222/391 |
| 5,007,755 | 4/1991 | Thompson | 401/175 |
| 5,019,375 | 5/1991 | Tanner et al. | 424/66 |
| 5,069,897 | 12/1991 | Orr | 424/66 |
| 5,102,656 | 4/1992 | Kasat | 424/66 |
| 5,156,834 | 10/1992 | Beckmeyer et al. | 424/47 |
| 5,169,626 | 12/1992 | Tanner et al. | 424/66 |
| 5,292,530 | 3/1994 | McCrea et al. | 424/66 |

OTHER PUBLICATIONS

German Patent Publication DE3150402 A 820708 (English Abstract) Derwent Acc. No. 82–57533E, Marschner, "Quick–drying powder suspensions".

Japanese Patent Publication JP 88–207564 (English Abstract) Chem. Abst. Plus., Higuchi, Naoo, "Deodorants for the skin and hair preparations".

ANTIPERSPIRANT CREAM COMPOSITIONS HAVING IMPROVED RHEOLOGY

This is a continuation-in-part of application Ser. No. 08/557,637, filed on Nov. 15, 1995, now abandoned and Ser. No. 08/557,249, filed on Nov. 14, 1995, now abandoned.

TECHNICAL FIELD

The present invention relates to antiperspirant cream compositions which provide improved spreading and product stability. In particular, the present invention relates to antiperspirant cream compositions having a select rheology that provides for improved product stability and application performance. The present invention also relates to methods for preparing such compositions.

BACKGROUND OF THE INVENTION

There are many types of topical antiperspirant products that are commercially available or otherwise known in the antiperspirant art. Most of those products are formulated as sprays, roll-on liquids, creams, or solid sticks, and comprise an astringent material, e.g. zirconium or aluminum salts, incorporated into a suitable topical carrier. These products are designed to provide effective perspiration and odor control while also being cosmetically acceptable during and after application onto the axillary area or other areas of the skin.

Within this product group, antiperspirant creams have become increasingly more popular as an effective alternative to antiperspirant sprays and solid sticks. These creams can be applied by conventional means, or packaged into topical dispensers to make topical application more efficient and less messy. Perspiration and odor control provided by these products can be excellent. Many of these creams, however, are cosmetically unacceptable to a large number of antiperspirant users. Application of these creams can be less messy, difficult to spread and wash off, and even when a cream applicator is employed, the applied areas often feel wet or sticky for several minutes after application. These compositions are especially difficult to uniformly spread over hairy areas of the skin. Many consumers have therefore preferred antiperspirant sticks for ease of administration and drier skin feel immediately after application, although the antiperspirant sticks typically leave an undesirably high residue on the skin.

One method for making improved antiperspirant creams involves the formulation of particulate antiperspirant actives in a mixture of volatile and nonvolatile silicones or other carriers. The use of such volatile solvents in these mixtures helps reduce stickiness, improve dry-down times after application onto skin, improve ease of spreading, and improve wash-off characteristics. To maintain physical stability of these creams, however, inorganic thickening agents such as bentonite clays, hectorite clays, colloidal or fumed silicas are often needed. The inorganic thickening agents, however, contribute a grainy texture to the product and are not especially effective in maintaining physical stability when higher concentrations of volatile silicone or nonsilicone solvents, or lower viscosity nonvolatile silicone or nonsilicone solvents are used. This physical instability results in solvent syneresis (weeping of solvent from the cream matrix) during packaging, storage or shipping.

Product instability in the form of solvent syneresis can be minimized or eliminated in these soft creams by simply formulating the product into a harder, more conventional, antiperspirant stick. Many consumers, however, prefer the lower residue cosmetics associated with the soft creams, especially when these creams are applied with a cream applicator device having a perforated cap through which the soft cream is extruded and applied to the skin. Antiperspirant sticks are too hard to be extruded through most perforated caps, and typically result in higher visible residue on the skin than soft antiperspirant creams.

Other methods of preparing soft antiperspirant creams involve compositions comprising a volatile silicone solvent, suitable gellant, and antiperspirant active, which compositions are prepared by select processing methods. Components of the compositions are mixed together and heated above the melt point of the gellant, and then cooled to below the normal solidification point of the composition while subjecting the composition to continuous mixing or shear. The continuous mixing or shear prevents the product from forming a solid matrix at its normal solidification point, and thus forms a soft creamy matrix with continuous mixing below its normal solidification point. The continuous mixing thus prevents the composition from solidifying into a harder gel stick, and thus transforms it into a soft cream instead. These compositions, however, tend to be physically unstable during storage and result in substantial solvent syneresis during storage, shipping or even during application of the soft cream when applied through a perforated cap.

It has now been found that new antiperspirant creams can be prepared that deliver improved cosmetics, product stability, and reduced solvent syneresis, without reliance on the use of inorganic or polymeric thickening agents. The new antiperspirant creams are anhydrous systems that are substantially free of inorganic or polymeric thickening agents, wherein the composition has a penetration force value of from about 75 grams-force to about 500 grams-force, a delta stress value of from about 300 dyne/cm$^2$ to about 8,000 dyne/cm$^2$ as measured after extrusion of the composition through a shear force delivery means, and a static yield stress value of at least about 1,000 dyne/cm$^2$ as measured after extrusion of the composition through a shear force delivery means. These creams are soft enough for application through a mesh top or other perforated application cap but act as antiperspirant sticks in having minimal or no syneresis during storage. When stress is applied to the new antiperspirant creams, preferably by extruding the cream through a perforated cap or other shear force delivery means, prior to application, the cream becomes more fluid-like and easier to apply topically to the skin. These improved creams are effective at maintaining product stability and minimizing solvent syneresis, especially when used in combination with higher concentrations of volatile solvents or lower viscosity nonvolatile solvents.

It has also been found that these anhydrous antiperspirant creams are especially effective when prepared by select processing methods. In particular, it has been found that these creams can be made by 1) preparing a flowable liquid composition containing from about 5% to about 35% by weight of a particulate antiperspirant active, from about 0.1% to about 20% by weight of a crystalline gellant, and from about 10% to about 80% of an anhydrous liquid carrier for the crystalline gellant having a solubility parameter of from about 3 to about 13; and 2) solidifying the flowable composition without application of continuous shear force at or beyond the point of solidification, wherein the solidified composition is substantially free or inorganic or polymeric thickening agents, and has a penetration force value of from about 75 gram-force to about 500 gram-force, a delta stress value of from about 300 dyne/cm$^2$ to about 8,000 dyne/cm$^2$ as measured after extrusion of the composition through a shear force delivery means, and a static yield stress value of at least about 1,000 dyne/cm² as measured after extrusion of the composition through a shear force delivery means.

It is therefore an object of the present invention to provide an anhydrous antiperspirant cream composition with improved stability and spreading performance that is substantially free of inorganic or polymeric thickening agents. It is yet another object of the present invention to provide such a composition in combination with a perforated cap or other shear force delivery means which provides for improved topical application of the composition onto skin. It is also an object of the present invention to provide a method for preparing such improved antiperspirant cream compositions.

SUMMARY OF THE INVENTION

The present invention is directed to anhydrous antiperspirant cream compositions that are substantially free of inorganic and polymeric thickening agents and have improved product stability and performance, which compositions have a penetration force value of from about 75 gram-force to about 500 gram-force, a delta stress value of from about 300 dyne/cm² to about 8,000 dyne/cm² as measured after extrusion of the composition through a shear force delivery means, and a static yield stress value of at least about 1,000 dyne/cm² as measured after extrusion of the composition through a shear force delivery means. These compositions preferably comprise from about 0.1% to about 20% by weight of a crystalline gellant, from about 10% to about 80% by weight of an anhydrous liquid carrier for the crystalline gellant having a solubility parameter of from about 3 to about 13, and from about 5% to about 35% by weight of a particulate antiperspirant active. The anhydrous composition contains less than 2% by weight of free or added water.

The present invention is also directed to a method for preparing the anhydrous antiperspirant cream compositions of the present invention that are substantially free or inorganic or polymeric thickening agents, which method comprises 1) preparing a flowable liquid having from about 5% to about 35% by weight of a particulate antiperspirant active, from about 0.1% to about 20% by weight of a crystalline gellant, and from about 10% to about 80% by weight of an anhydrous liquid carrier for the crystalline gellant having a solubility parameter of from about 3 to about 13, and then 2) solidifying the flowable liquid without application of shear, mixing or agitation after the point of solidification of the flowable liquid, wherein the solidified composition has a penetration force value of from about 75 gram-force to about 500 gram-force, a delta stress value of from about 300 dyne/cm² to about 8,000 dyne/cm² as measured after extrusion of the composition through a shear force delivery means, and a static yield stress value of at least about 1,000 dynes/cm² as measured after extrusion of the composition through a shear force delivery means.

DETAILED DESCRIPTION OF THE INVENTION

Figure 1:
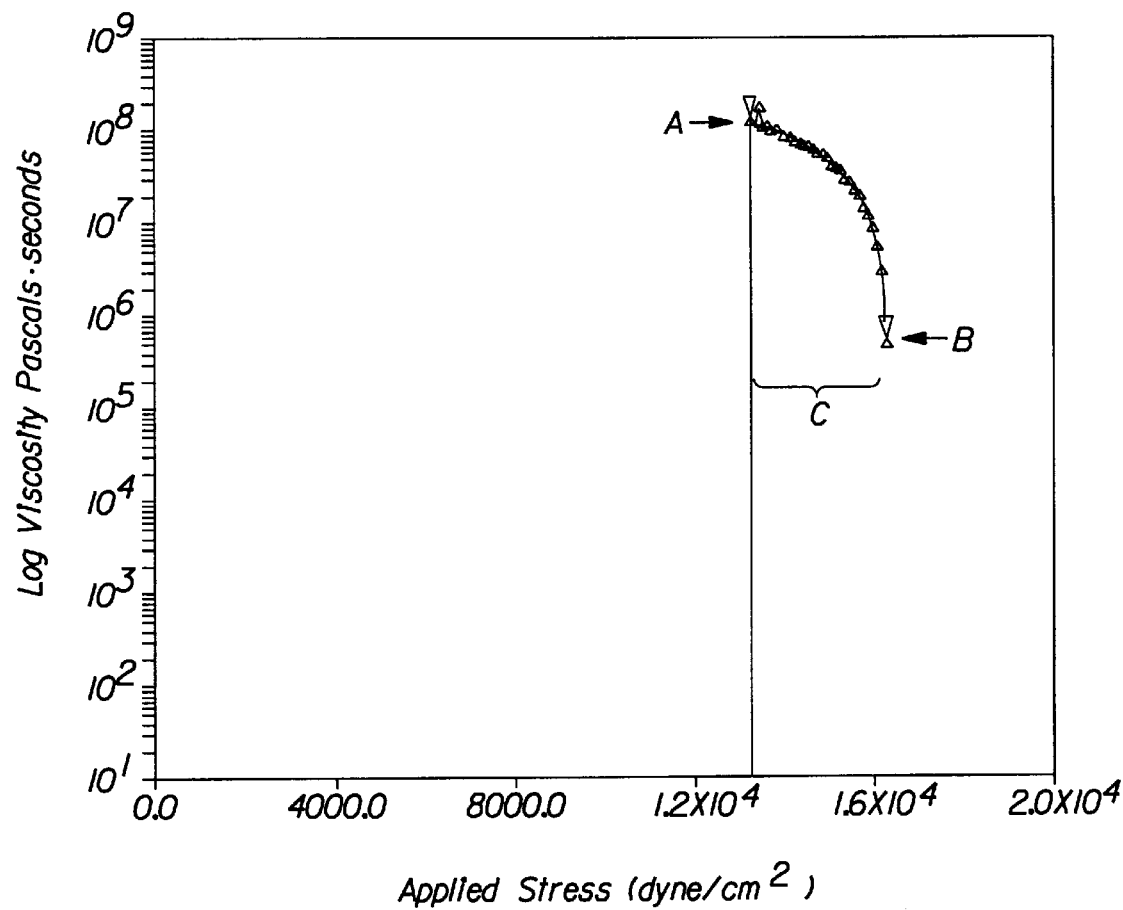
FIG. 1 is a graph which shows the static yield stress and delta stress values of an antiperspirant cream composition of the present invention (Example I) after extrusion through the perforated cap shown in FIGS. 2A, 2B and 2C. The vertical axis represents product viscosity (pascal-sec.) as measured by Rheometrics Dynamic Stress Rheometer. The horizontal axis represents applied stress (dyne/cm²) to the composition. For the sample composition, the graph shows a static yield stress value (point "A" on horizontal axis) of about 13,200 dyne/cm², a dynamic yield stress value (point "B" on horizontal axis) of about 16,200 dyne/cm², and a delta stress value (interval "C" of the horizontal axis) of about 3,000 dyne/cm².

The antiperspirant cream compositions of the present invention are dispersions of particulate antiperspirant solids in a continuous water-insoluble or lipophilic phase. These compositions are anhydrous systems which are suitable for use in topical cream applicators, or by other known or otherwise effective means of topically applying a cream to the skin.

The term "anhydrous" as used herein means that the antiperspirant cream composition of the present invention, and the essential or optional components thereof, are substantially free of added or free water. From a formulation standpoint, this means that the antiperspirant cream compositions of the present invention contain less than about 2%, preferably less than about 1%, more preferably less than about 0.5%, more preferably zero percent, by weight of free or added water. The "anhydrous liquid carrier s" described hereinafter likewise contain no more that the above described percentages of free or added water.

The term "shear force delivery means" as used herein refers to any perforated cap, mesh top, or other surface having openings, apertures or orifices through which the antiperspirant cream composition of the present invention can be extruded, and that during such extrusion, the shear force delivery means subjects the composition to shear that is generally insufficient to substantially liquefy the composition, preferably a shear force less than the dynamic stress value of the composition, more preferably a shear force less than the static stress value of the composition. Examples of such shear force delivery means are known in the art, and are also described in greater detail hereinafter.

The term "ambient conditions" as used herein refers to surrounding conditions under about one atmosphere of pressure, at about 50% relative humidity, at about 25° C.

The term "crystalline gellant" as used herein means nonpolymeric gellants, and includes crystalline as well as noncrystalline gellants that can be used to form a gellant matrix within the composition that provides the requisite rheology characteristics defined herein. Most preferred are gellant materials in crystalline form.

The term "substantially free of polymeric or inorganic thickening agents" as used herein refers to the antiperspirant cream compositions of the present invention, and means that the compositions contain less than an effective amount of such agents when used alone to provide any thickening or measurable viscosity increase to the composition. In this context, the polymeric and inorganic thickening agents refer only to materials that are solid under ambient conditions. Generally, the compositions preferably contain less than 5%, preferably less than 2%, more preferably less than 1%, even more preferably less than 0.5%, most preferably zero percent, of such thickening agents by weight of the compositions. Examples of inorganic thickening agents to which the above-described negative limitations pertain include finely divided or colloidal silicas, fumed silicas, and silicates, which includes montmorillonite clays and hydrophobically treated montmorillonites, e.g., bentonites, bectorites and colloidal magnesium silicates. Examples of polymeric thickening agents to which the above-described negative limitations pertain include polymers well known in the antiperspirant or personal care art for use in providing thickening benefits to a composition, specific examples of which include hydrogenated butylene/ethylene/styrene copolymer, polyethylene, acrylic acid polymers, ethylene acrylate copolymers, and other polymeric thickening agents described in Rheological Properties of Cosmetics and Toiletries, Edited by Dennis Laba, published by Marcel Dekker, In., New York (1993), which description is incorporated herein by reference. All such excluded polymeric and inorganic thickening agents are solids under ambient conditions.

The antiperspirant cream compositions of the present invention can comprise, consist of, or consist essentially of the essential elements and limitations of the invention described herein, as well as any of the additional or optional ingredients, components, or limitations described herein.

As percentages, parts and ratios are by weight of the total composition, unless otherwise specified. All such weights as they pertain to listed ingredients are based on the active level and, therefore, do not include solvents or by-products that may be included in commercially available materials, unless otherwise specified.

EXAMPLES

The antiperspirant cream compositions of the present invention are anhydrous creams which have a select rheology profile that helps improve product stability and performance. The rheology profile as defined herein is a combination of select product hardness (penetration force), delta stress (dyne/cm$^2$) and static yield stress (dyne/cm$^2$) values for the antiperspirant cream composition. Methods for measuring or determining each of these essential characteristics of the rheology profile are described in detail hereinafter. Rheology methodologies are carried out at 27° C., 15% relative humidity, unless otherwise specified.

1. Methodology; Delta Stress and Static Yield Stress

To determine delta stress and static stress yield values for the antiperspirant cream compositions herein, the compositions are analyzed using a Rheometrics Dynamic Stress Rheometer (available from Rheometrics Inc., Piscatawany, N.J., U.S.A.) with data collection and analysis performed using Rhios software 4.2.2 (also available from Rheometrics Inc., Piscatawany, N.J., U.S.A.). The rheometer is configured in a parallel plate design using a 25 mm upper plate (available as part number LS-PELT-IP25 from Rheometrics Inc., Piscatawany, N.J., U.S.A.). Temperature control is set at 37° C. Analysis of the antiperspirant cream is performed in the "Stress Sweep: steady sweep" default test mode. Rheometer settings are initial stress (1.0 dyne/cm$^2$), final stress (63,930 dyne/cm$^2$), stress increment (100 dyne/cm$^2$), and maximum time per data point (5 seconds).

The term "static yield stress" as used herein refers to the minimum amount of stress ( dyne/cm$^2$) that must be applied to the antiperspirant composition to move the upper plate of the Rheometrics Dynamic Stress Rheometer a distance of about 4.2 micro radians, in accordance with the analysis methods described herein. In other words, static yield stress represents the point in a stress sweep analysis (described herein) of a product at which point the rheometer is first capable of measuring product viscosity.

The term "delta stress" as used herein is determined by subtracting the static yield stress from the dynamic yield stress of a composition. The dynamic yield stress is the point at which the measured viscosity begins to rapidly decline. This can be easily determined by finding the last stress value where the increment between stress values is 100 dynes/cm$^2$. In other words, the delta stress of the composition represents the incremental amount of stress that must be applied to the composition, beyond the static yield stress of the composition, to substantially liquefy the composition after extrusion.

The antiperspirant cream composition is first evaluated for rheology characteristics before extrusion (e.g., evaluation of a packaged product) through a defined perforated cap. A 28 gauge metal wire is used to slice of a thin section (about 1 mm thick) from the packaged antiperspirant cream. During and after slicing, care is taken so that the product slice is subjected to minimal shear, and especially that it is not permitted to curl or otherwise reconfigure to a shape other than that of the section as it was removed from the packaged composition. The section is carefully placed flat on the lower plate of the rheometer taking care to minimize the application of shear stress on the section during the placement. The area of the placed section is at least about the size of the upper plate to assure proper contact between the two plates during testing. The upper plate is then lowered toward the bottom plate, and positioned about 2 mm above the lower plate, and therefore about 1 mm from the product section which is positioned flat on the lower plate. The upper plate is further lowered at a minimal rate toward the lower plate, and positioned about 1,000 (±0.002) mm above the lower plate, at which point the product slice is gently positioned between and contacting each of the lower and upper plates. Excess product extending away from and around the parallel positioned plates is gently removed using a spatula, and taking care to subject the product positioned between plates to minimal or no further shear from the spatula. The solvent guard pad on the rheometer is saturated with the type of anhydrous liquid carrier corresponding to that in the test product. The solvent guard is lowered over the parallel plates to prevent solvent loss from the test product that is positioned between the plates during analysis. The product is now ready for rheology analysis and determination of dynamic stress, static yield stress, and delta stress.

The antiperspirant cream composition is also evaluated for rheology characteristics immediately after the composition is extruded through a perforated cap. The perforated cap used in this analysis has the general configuration of the perforated mesh cap shown in FIGS. 2A, 2B and 2C. To prepare product for such an evaluation, the product is first extruded through the perforated until from about 1 to about 3 mm of product extends from the exterior of the perforated cap. Gently remove extruded product from the surface of the cap using a spatula and place the removed product in the center of the lower plate, all along being careful to subject the product to minimal or no shear. Product should have an area at least about the size of the upper plate to assure proper contact between the two plates. The upper plate is lowered to about 2 mm, and then at a minimal rate further lowered to about 0.500 (±0.002) mm. Excess product extending away from and around the parallel positioned plates is gently removed using a spatula, and again taking care to subject the product positioned between plates to minimal or no further shear from the spatula. The solvent guard is lowered over the parallel plates to prevent solvent loss during analysis. The solvent guard should be saturated with anhydrous liquid carrier corresponding to the type of carrier in the test product prior to placement of test product on the instrument. The extruded product thus positioned between the parallel plates is now ready for rheology analysis and determination of dynamic stress, static yield stress, and delta stress.

Product samples before extrusion and product samples after extrusion through the perforated cap are subjected to rheological test and evaluation in accordance with the above described methodology. Data from the above described analysis can be plotted as viscosity)pascal-sec.) on a log scale versus linear applied stress (dyne/cm$^2$), an example of which is shown in FIG. 1 herein. The initial point at which the instrument measures a viscosity is the static yield stress (i.e. the lowest stress at which the instrument shows a non-zero viscosity). The dynamic yield stress is the point at which the measured viscosity begins to rapidly decline. This can be easily determined by finding the last stress value where the increment between stress values is 100 dynes/cm$^2$. The delta stress is then determined by subtracting the static yield stress from the dynamic yield stress.

2. Methodology; Product Hardness

The antiperspirant cream compositions of the present invention are evaluated for product hardness (gram-force) and defined in terms of force penetration values. The penetration force values are a reflection of how far a defined penetration cone will penetrate through an antiperspirant cream composition under the following test conditions. Higher values represent harder product, and lower values represent softer product. These values are measured at 27° C., 15% relative humidity, using a TA-XT2 Texture Analyzer, available from Texture Technology Corp, Scarsdale, N.J., U.S.A. The penetration force value as used herein represents the force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weights about 17.8 grams.

3. Rheology Profile

The antiperspirant cream compositions of the present invention have a select rheology profile defined by three essential rheology characteristics—select product hardness, static yield stress, and delta stress. As to the first essential rheology characteristic, the product hardness of the composition is characterized as a penetration force value of from about 75 gram-force to about 500 gram-force, preferably from about 100 gram-force to about 400 gram force, more preferably from about 150 gram-force to about 250 gram force.

The second essential rheology characteristic of the antiperspirant cream compositions is a static yield stress value as measured after extrusion of the composition through a shear force delivery means, and preferably as also measured prior to such extrusion. The compositions have a static yield stress value as measured after extrusion of at least about 1,000 dyne/cm$^2$, preferably at least about 3,000 dyne/cm$^2$, even more preferably at least about 4,000 dyne/cm$^2$, and most preferably at least about 10,000 dyne/cm$^2$. The composition preferably also has a maximum static yield stress value as measured after extrusion of less than about 63,000 dyne/cm$^2$, more preferably less than about 35,000 dyne/cm$^2$.

The compositions also preferably have a static yield stress value prior to extrusion of at least about 4,000 dyne/cm$^2$, more preferably at least about 8,000 dyne/cm$^2$, even more preferably at least about 40,000 dyne/cm$^2$. The maximum static yield stress values for the composition prior to extrusion are preferably less than about 120,000 dyne/cm$^2$, more preferably less than about 63,000 dyne/cm$^2$.

Highly preferred are compositions having a static yield stress value as measured after extrusion of from about 4,000 dyne/cm$^2$ to about 35,000 dyne/cm$^2$. Also highly preferred are compositions having a static yield stress as measured prior to extrusion of from about 4,000 dyne/cm$^2$ to about 63,000 dyne/cm$^2$.

Products with a static yield stress value below the minimum levels recited herein can shear thin too much prior to application by the end user, or are otherwise physically unstable, especially during extended storage in a closed applicator package or during rough shipping to distributors or consumers. This product instability or excessive thinning of the product matrix can result in solvent syneresis from the composition during packaging, shipping or extended storage.

The second essential rheology characteristic of the antiperspirant cream compositions is a select range of delta stress values, wherein the delta stress values are measured either prior to or after extrusion through a shear force delivery means. The delta stress value of the composition is from about 300 dyne/cm$^2$ to about 8,000 dyne/cm$^2$, preferably from about 1,000 dyne/cm$^2$ to about 6,000 dyne/cm$^2$, more preferably from about 1,000 dyne/cm$^2$ to about 5,000 dyne/cm$^2$. A delta stress below the minimum level can result in solvent syneresis during extrusion through a perforated cap or other shear force delivery means, whereas a value above the recited maximum can result in product fracture during extrusion, nonuniform spreading onto the skin, and reduced spreadability on the skin, especially on hairy areas of the skin. Syneresis during extrusion of the composition through a perforated cap results in a separated, messy and excessively liquid composition being delivered topically to the skin. The delta stress values, therefore, recited herein provide for improved flow of the antiperspirant cream through a perforated cap or other shear force delivery means, and furthermore provides for a smooth creamy product after extrusion that shows minimal or no solvent syneresis, spreads uniformly over the skin, and spreads especially well over and through hairy areas of the skin.

The compositions of the present invention are preferably characterized in terms of delta stress and yield stress values after extrusion of the composition, although the compositions can alternatively be characterized in terms of delta stress and yield stress values prior to such extrusion. The compositions can also be characterized in terms of delta stress and yield stress values before and after extrusion.

Figure 2A:
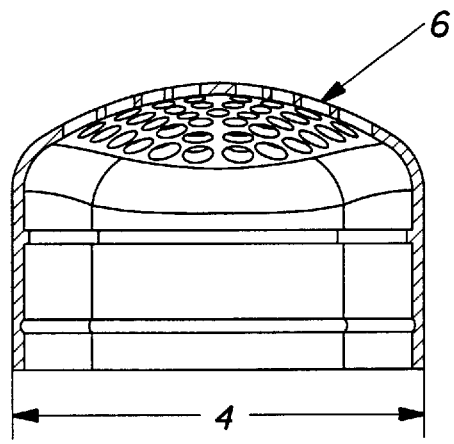
FIGS. 2A, 2B and 2C illustrate is a perforated or mesh top which is a preferred shear force delivery means for use herein. The mesh top illustrated in FIGS. 2A, 2B and 2C is also used in the rheology methodology described herein for defining delta stress and static yield stress values of compositions after extrusion through a shear force delivery means. The mesh top has circular apertures (1) having diameters of 2.5, 2.4, and 1.9 mm; aperture spacing (2) of from 0.76 to 1.8 mm; a dome major axis (3) of 52.1 mm; a dome minor axis (4) of 33.0 mm; a dome radius of curvature (5) (major) of 57.1 mm; a dome radius curvature (6) (minor) of 22.9 mm; and a dome thickness (7) of from 0.79 mm to 0.89 mm.
Figure 2B:
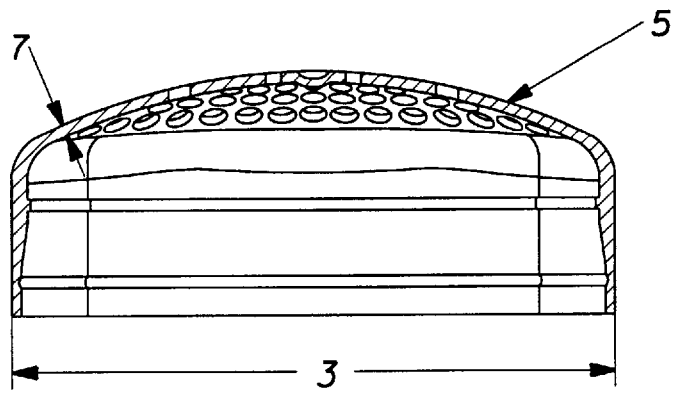
Figure 2C:
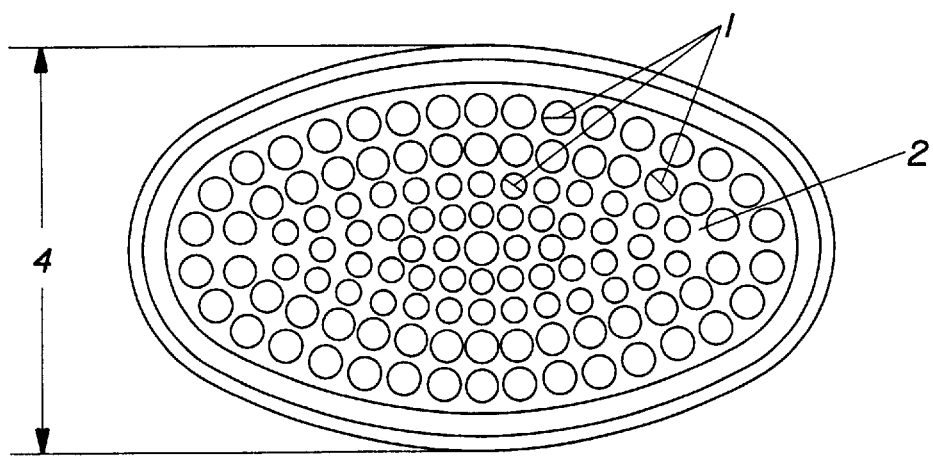

For purposes of defining the antiperspirant cream composition of the present invention, the delta stress and static yield stress characteristics for extruded compositions are measured in accordance with the rheology methodology described herein. Such methodology requires a shear force delivery means having the general mesh top configuration as illustrated in FIGS. 2A, 2B and 2C wherein the mesh cap has circular apertures in the illustrated configuration having diameters of 2.5, 2.4, and 1.9 mm; aperture spacing of from 0.76 to 1.8 mm; a dome major axis of 52.1 mm; a dome minor axis of 33.0 mm; a dome radius of curvature (major) of 57.1 mm; a dome radius curvature (minor) of 22.9 mm; and a dome thickness of from 0.79 mm to 0.89 mm.

It has been found that by controlling the rheology profile of the antiperspirant cream composition to within the narrow ranges described herein, this provides a means for improving product stability, aesthetics, and performance in an anhydrous antiperspirant composition without reliance on polymeric or inorganic thickening agents.

Antiperspirant Active

The antiperspirant cream compositions of the present invention comprise a particulate antiperspirant active suitable for application to human skin. Suitable actives for use in the compositions are those which remain substantially unsolubilized as dispersed solid particulates in an anhydrous or substantially anhydrous system. The concentration of active in the composition should be sufficient to provide the desired odor and wetness control from the antiperspirant cream formulation selected.

The antiperspirant cream compositions of the present invention preferably comprise the antiperspirant active particles at concentrations of from about 5% to about 35%, more preferably from about 10% to about 30%, by weight of the composition. These weight percentages are calculated on an anhydrous metal salt basis exclusive of water and any complexing agents such as glycine, glycine salts, or other complexing agents. The antiperspirant active particles as formulated in the composition are in the form of dispersed solid particles having a preferred average particle size or diameter of from about 1 $\mu$m to about 100 $\mu$m, more preferably from about 1 $\mu$m to about 50 $\mu$m.

The antiperspirant active for use in the antiperspirant cream compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum hydroxyhalides, zirconyl oxyhalides, zirconyl hydroxyhalides, and mixtures thereof.

Preferred aluminum salts for use in the antiperspirant cream composition include those which conform to the formula:

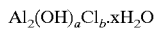

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5 and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant cream composition include those which conform to the formula:

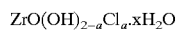

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britian Patent Application 2,144,992, Callaghan et al., published Mar. 20, 1985; and U.S. Pat. No. 4,120,948, Shelton, issued Oct. 17, 1978, all of which are incorporated herein by reference.

The anhydrous cream composition of the present invention can also be formulated to comprise other dispersed solids or other materials in addition to or in place of the antiperspirant active particles. Such other dispersed solids or other materials include any material known or otherwise suitable for topical application to human skin. The anhydrous cream composition can also be formulated as a cosmetic cream which contains no active materials, particulate or otherwise.

Gellant

The antiperspirant cream compositions of the present invention preferably comprise one or more solid crystalline or other nonpolymeric gellant suitable for topical application to human skin. Suitable gellants are those which can form in the composition a crystalline or other gellant matrix within which a liquid carrier or other liquid component of the composition are contained.

The concentration of the gellants in the composition may vary with each selected antiperspirant cream formulation, especially with each selected anhydrous liquid carrier of the formulation, but such concentrations will generally range from about 0.1% to about 20%, preferably from about 1% to about 15%, more preferably from about 3% to about 12%, by weight of the composition.

Suitable gellants for use in the composition are solids under ambient conditions. These solid gellants preferably have a melting point of from 60° C. to about 140° C., preferably from about 60° C. to about 120° C., more preferably from about 70° C. to about 110° C. The solid gellant will typically and preferably be a crystalline material. Likewise, the gellant matrix in the composition will typically and preferably be a crystalline matrix.

The gellants for use in the antiperspirant cream compositions are those which can melt and form a homogenous liquid or homogenous liquid dispersion with the selected anhydrous liquid carrier, and at the selected gellant and liquid carrier concentrations, at a processing temperature of from about 28° C. to about 125° C. The melted gellant is typically dispersed throughout the selected liquid carrier to thus form a homogenous liquid. The homogenous liquid, and other essential and optional ingredients, are preferably combined in accordance with the manufacturing method herein, placed in a suitable package as a flowable homogenous liquid, and then allowed to solidify and form the desired gellant matrix within the composition as the temperature returns to ambient temperature and drops to below the solidification point of the selected gellant.

In selecting a combination of gellant and liquid carrier for use in the antiperspirant cream compositions, the selected combination must allow for the development of a gellant matrix within the composition that will help deliver the requisite delta stress and static yield stress values described herein. The liquid carrier and gellant combination must also be selected so as to formulate a composition having the requisite product hardness, with minimal or no destruction of the gellant matrix as it develops within the antiperspirant cream composition during the making process. Maintaining the gellant matrix as it develops in the composition is important to obtaining the desired rheology profile defined herein, especially delta stress and static yield stress values. The liquid carrier and gellant combination should also be selected so as to assist in minimizing gellant crystal particle size within the antiperspirant cream composition. Methods for minimizing gellant particle size in various compositions are known generally in the art, and the control of such particle size to help achieve the desired rheology characteristics is easily accomplished by one of ordinary skill in the art without undue experimentation.

Gellants for use in the antiperspirant composition include fatty alcohols, esters of fatty alcohols, fatty acids, amides of fatty acids, esters of ethers of fatty acids including triglycerides, ethoxylated fatty alcohols, ethoxylatd fatty acid, corresponding salts thereof, combinations thereof, and other crystalline gellants known or otherwise effective in providing the desired crystalline matrix within the antiperspirant composition. All such gellants preferably have a fatty alkyl moiety having from about 14 to about 60 carbon atoms, more preferably from about 20 to about 40 carbon atoms, and which may be saturated or unsaturated, substituted or unsubstituted, branched or linear or cyclic. Preferred fatty alkyl moieties are saturated, more preferably saturated and unsubstituted.

The term "substituted" as used herein refers to chemical moieties known or otherwise effective for attachment to gellants or other compounds. Such substituents include those listed and described in C. Hansch and A. Leo, *Substituent Constants for Correlation Analysis in Chemistry and Biology* (1979) which listing and description are incorporated herein by reference. Examples of such substituents include, but are not limited to, alkyl, alkeny, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

The term "corresponding salts" as used herein refers to cationic salts formed at any acidic (e.g., carboxyl) group, or anionic salts formed at any basic (e.g., amino) group, either of which are suitable for topical application to human skin. Many such salts are known in the art, examples of which are described in World Patent Publication 87/05297, Johnston et al., published Sep. 11, 1987, which description is incorporated herein by reference.

Nonlimiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty alcohols may be used in the composition at concentrations preferably ranging from about 0.1% to about 8%, more preferably from about 3% to about 8%, even more preferably from about 3% to about 6%, by weight of the composition. The fatty alcohol gellants are also preferably saturated, unsubstituted, monohydric alcohols or combinations thereof, which have a melting point preferably less than about 110° C. Specific examples of fatty alcohol gellants for use in the antiperspirant compositions that are commercially available include, but are not limited to, Unilin 550, Unilin 700, Unilin 425, Unilin 400, Unilin 350, and Unilin 325, all supplied by Petrolite.

Suitable ethoxylated gellants include, but are not limited, Unithox 325, Unithox 400, and Unithox 450, Unithox 480, Unithox 520, Unithox 550, Unithox 720, Unithox 750, all of which are available from Petrolite.

Suitable fatty acid esters for use as crystalline gellants include ester waxes, monoglycerides, diglycerides, triglycerides and combinations thereof. Preferred are the glyceride esters. Nonlimiting examples of suitable ester waxes including stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Keater waxes from Koster Keunen, Crodamol SS from Crode and Demalcare SPS from Rhone Poulenc.

Preferred are glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant preferably has a preferred melting point of less than about 110° C. Preferred concentrations of the triglyceride gellants in the antiperspirant composition range from about 4% to about 20%, more preferably from about 4% to about 10%, by weight of the composition. Specific examples of preferred triglyceride, gellants inlcude but are not limited to, tristearin, tribehenate, behenyl palmityl behenyl triglyceride, palmityl stearyl palmityl triglyceride, hydrogenated vegetable oil, hydrogenated rape seed oil, castor wax, fish oils, tripalmiten, Syncrowax HRC and Syncrowax HGL-C (Syncrowax is available from Caroda, Inc.). Other suitable glycerides include, but are not limited to, and glyceryl stearate and glyceryl distearate.

Suitable amide gellants include monoamide gellants, diamide gellants, triamide gellants, and combinations thereof, nonlimiting examples of which include cocoamide MEA (monoethanolamide), stearamide, oleamide, oleamide MEA, tallow and monoethanolamide, and the n-acyl amino acid amide derivatives described in U.S. Pat. No. 5,429,816, issued to Hofrichter et al. on Jul. 4, 1995, which description is incorporated herein by reference.

Suitable fatty acid gellants include, but are not limited to, 12-hydroxystearic acid and derivatives thereof, behenic acid, eurcic acid, stearic acid, C20 to C40 fatty acids, and related gellants, some preferred examples of which are disclosed in U.S. Pat. No. 5,429,816, issued to Hofrichter et al. on Jul. 4, 1995; and U.S. Pat. No. 5,552,136, issued to Motley on Sep. 3, 1996, both disclosures of which are incorporated by reference herein. Some commercial examples of fatty acid gellants include, but are not limited to, Unicid 400, available from Petrolite.

Preferred crystalline gellants for use in the antiperspirant composition include coconut monoethanolamide, glyceryl tribehenate, C18–36 triglyceride, hydrogenated rapeseed oil, C20 to C40 alcohols, C20 to C40 pareth-3 and combinations thereof. Concentration of coconut monoethanolamide in the composition preferably ranges from about 5% to about 20%, more preferably from about 5% to about 15%, by weight of the composition. Coconut monoethanolamide is especially preferred when used in compositions containing a volatile silicone solvent, especially volatile cyclomethicone, and in compositions containing a combination a volatile silicone carrier and a nonvolatile silicone (e.g., nonvolatile dimethicones) or a nonvolatile organic carrier.

Glyceryl tribehenate and hydrogenated rapeseed oil are also preferred gellants when used in gellant systems containing C20 to C40 fatty alcohols and/or C20 to C40 pareth-3, wherein the weight ratio of glyceryl tribehenate or hydrogenated rapeseed oil to C20 to C40 fatty alcohols and/or C20 to C40 pareth-3 is from about 20:1 to about 1:1, preferably from about 10:1 to about 3:1. These gellants are especially preferred when used in compositions containing volatile silicone carrier, especially volatile cyclomethicone, and in compositions containing a combination of a volatile silicone carrier and a nonvolatile silicone (e.g., nonvolatile dimethicones) or a nonvolatile organic carrier.

Some of the crystalline gellants suitable for use in the antiperspirant cream composition herein are also described in U.S. Pat. No. 5,552,136, issued to Motley on Sep. 3, 1996; and U.S. Pat. No. 5,429,816 issued to Hofrichter et al. on Jul. 4, 1995; which descriptions are incorporated herein by reference.

It has been found that many crystalline gellants are suitable for use in the antiperspirant cream composition of the present invention, provided that the gellant can be formulated to form a crystalline matrix within the composition, which in turn provides the essential rheology profile (delta stress, static yield stress, penetration force) described herein for delivering the product spreading and stability benefits also described herein. In particular, the selected gellant should be combined with an appropriate anhydrous liquid carrier and formulated into the composition so as to form crystallized gellant forming a crystalline matrix, wherein the size of the gellant crystals in the matrix are minimized. It is also important that the formulation results in the development of a crystalline matrix within the composition with minimal or no application of any shear force that might otherwise break down the structure of the matrix. Preferred methods for preparing these crystalline matrices within the composition are described in detail hereinafter.

The gellant material in the composition preferably has an average particle size within the crystalline matrix of less than about 10 µm, more preferably from about 0.1 µm to about 5 µm, even more preferably from about 1 µm to about 4 µm. It has been found that these smaller crystalline particles are especially effective in developing the rheology model of the composition described herein. These smaller particles form an improved crystalline matrix within which the dispersed particulate antiperspirant active is physically held in place over extended periods, and within which the anhydrous liquid carrier component of the composition is held with minimal syneresis during storage, transport and extrusion through a perforated cap.

Anhydrous Liquid Carrier

The anhydrous antiperspirant cream compositions of the present invention comprise an anhydrous liquid carrier for the crystalline gellant described hereinbefore, wherein the anhydrous liquid carrier comprises one or more liquid carriers each or collectively having a solubility parameter of from about 3 to about 13, preferably from about 5 to about 11, more preferably from about 5 to about 9. The term "liquid carrier" and "carrier" are used interchangeably herein, and refer to the anhydrous liquid carrier component of the composition, which forms a homogenous liquid with the selected gellant as describer herein.

Solubility parameters for selected liquid carrier s or other materials, and means for determining such parameters, are well known in the antiperspirant art. A description of solubility parameters and means for determining them are described in C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J Soc. Cosmetic Chemists 319–333, September/October, 198, which descriptions are incorporated herein by reference.

Concentrations of the anhydrous liquid carrier the composition will vary with the type of liquid carrier selected, the type of gellant used in combination with the liquid carrier, and the solubility of the selected gellant in the selected carrier, and so forth. Preferred concentrations of the anhydrous liquid carrier ranges from about 10% to about 80%, preferably from about 30% to about 70%, more preferably from about 45% to about 70%, by weight of the composition.

The anhydrous liquid carrier comprises one or more liquid carrier s suitable for topical application to human skin, which carrier or combination of liquid carrier s are liquid under ambient conditions. These liquid carrier s may be organic or silicone-containing, volatile or nonvolatile, polar or nonpolar, provided that the carrier can form a homogenous liquid or homogenous liquid dispersion with the selected gellant at the selected gellant concentration at a temperature of from about 28° C. to about 125° C. The anhydrous liquid carrier preferably has a low viscosity to provide for improved spreading performance on the skin, more preferably less than about 50 cs (centistokes), even more preferably less than about 10 cs.

The anhydrous liquid carrier preferably comprises one or more volatile carriers, optionally in combination with a nonvolatile carrier. In this context, the term "volatile" refers to carriers having a measurable vapor pressure under ambient conditions, and the term "nonvolatile" refers to carriers which do not have a measurable vapor pressure under ambient conditions.

Preferred volatile liquid carrier s are the volatile silicone carriers, which includes cyclic, linear or branched chain volatile silicones. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred volatile silicone materials are those having from about 3 to about 7, more preferably from about 4 to about 5, silicon atoms. Cyclic silicones are preferred.

Suitable cyclic silicones for use in the antiperspirant cream composition include those volatile silicones which conform to the formula:

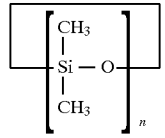

wherein n is from about 3 to about 7, preferably from about 4 to about 5, more preferably 5. These cyclic silicone materials will generally have viscosity values of less than about 10 cs at ° C.

Suitable linear silicones suitable for use in the antiperspirant cream compositions include those volatile linear silicones which conform to the formula:

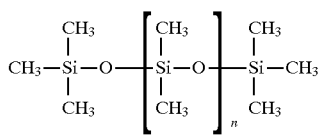

wherein n is from about 1 to about 7, preferably from about 2 to about 3. These linear silicone materials will generally have viscosity values of less than about 5 cs at 25° C.

Specific examples of volatile silicone carriers suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicone Corp.).

Other suitable carriers for use in the composition include nonvolatile silicone emollients, preferably low viscosity nonvolatile silicone carriers having a viscosity of less than about 500 cs, more preferably from about 5 cs to about 50 cs, more preferably from about 5 cs to about 20 cs. These silicone emollients include, but are not limited to, polyalkylsiloxanes, polyalkyarylsiloxanes and polyethersiloxane copolymers. Examples of such emollients are well known in the art, some of which are described in 1 *Cosmetics, Science and Technology* 27–104 (M. Balsam and E. Sagarin ed. 1972); U.S. Pat. No. 4,202,879, issued to Shelton on May 13, 1990; and U.S. Pat. No. 5,069,987, issued to Orr on Dec. 3, 1991; which descriptions are incorporated herein by reference.

Organic carriers for use in the composition include saturated or unsaturated, substituted or unsubstituted, branched or linear cyclic, organic compounds that are also liquid under ambient conditions. These carriers include hydrocarbon oils, alcohols, organic esters and ethers that are liquid under ambient conditions. Preferred organic carriers include mineral oil and other hydrocarbon oils, some examples of which are described in U.S. Pat. No. 5,019,375, issued to Tanner et al. on May 28, 1991, which description is incorporated herein by reference. Other suitable organic liquid carriers include Permethyl 99A, Permethyl 101A (Permethyl available from Permethyl Corp.), Isopar M, Isopar V (Isopar available from Exxon), isohexadecane, disopropyl adipate, butyl stearate, isododecane, light mineral oil, petrolatum and other similar materials.

Optional Components

The antiperspirant compositions of the present invention may further comprise one or more optional components which may modify the physical or chemical characteristics of the compositions or serve as additional "active" components when deposited on the skin. The compositions may also further comprise optional inert ingredients. Many such optional materials are known in the antiperspirant art and may be used in the antiperspirant compositions herein, provided that such optional materials are compatible with the essential materials described herein, or do not otherwise unduly impair product performance.

Non limiting examples of optional materials include active components such as bacteriostats and fungiostats, and "non-active" components such as colorants, perfumes, emulsifiers, chelants, distributing agents, preservatives, residue masking agents, and wash-off aids. Examples of such optional materials are described in U.S. Pat. No. 4,049,792, Elsnam, issued Sep. 20, 1977; Canadian Patent 1,164,347, Beckmeyer et al., issued Mar. 27, 1984; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

Packaged Composition

The antiperspirant cream composition of the present invention preferably further comprises a packaged delivery system having a shear force delivery means. Examples of such delivery systems are well known in the art, and typically comprise an enclosed package or container having an attached shear force delivery means such as a perforated cap or other perforated surface.

The shear force delivery means includes any ridged or flexible surface, preferably a ridged surface, suitable for attachment to a package or other product, and which has a plurality of openings, apertures or orifices extending through the thickness of the ridged or flexible surface through which the composition can flow to the intended site of application. The ridged or flexible surface preferably has a rounded, convex configuration having a radius of curvature of from about 25 mm to about 127 mm, preferably from about 57 mm to about 69 mm, for a major dimension; a radius of curvature of from about 12 mm to about 39 mm, preferably from about 22 mm to about 28 mm for a minor dimension; average aperture diameter of from about 1.9 mm to about 2.6 mm, preferably from about 0.6 mm to about 26 mm; average aperture spacing of from about 0.25 mm to about 13 mm, preferably from about 0.7 mm to about 23 mm; a surface or dome thickness of from about 0.25 mm to about 1.53 mm, preferably from about 0.7 mm to about 0.97 mm; a dome major axis of from about 38 mm to about 77 mm, preferably from about 52 mm to about 69 mm; and a dome minor axis of from about 12 mm to about 51 mm, preferably from about 18 mm to about 40 mm. Most preferred is the rounded perforated mesh top illustrated in FIGS. 2A, 2B and 2C hereof.

In particular, the packaged anhydrous antiperspirant cream composition of the present invention comprises any of the antiperspirant cream compositions described hereinbefore, but preferably comprises from about 5% to about 35% by weight of a particulate antiperspirant active; from about 0.1% to about 20% by weight of a crystalline gellant; from about 10% to about 80% by weight of an anhydrous liquid carrier for the crystalline gellant material, the anhydrous liquid carrier having a solubility parameter of from about 3 to about 13; and a shear force delivery means which provides shear to the composition during extrusion from the package and prior to topical application of the composition to the skin; wherein the antiperspirant cream composition has a penetration force value of from about 75 gram-force to about 500 gram-force, a delta stress value of from about 300 dyne/cm$^2$ to about 8000 dyne/cm$^2$ before or after extrusion through a shear force delivery means, and a static yield stress value after extrusion through a shear force delivery means of at least about 1,000 dyne/cm$^2$. The packaged composition more preferably comprises the preferred embodiments of the antiperspirant cream compositions described herein.

It has been found that the antiperspirant cream composition of the present invention is particularly effective when combined with a shear force delivery means such as a perforated cap. The shear force delivery means, when applied to the compositions having the selected rheology profile described herein, helps provide improved spreading of the applied composition to the skin, especially to hairy areas of the skin. The product applies more uniformly over the skin and through axilla hair, which results in improved deodorant and antiperspirant control. Moreover, the compositions of the present invention exhibit minimal or no solvent syneresis during extrusion through a perforated cap or other delivery means.

Examples of suitable perforated caps or other shear force delivery means for use in the packaged composition of the present invention include those known in the art for application of creams, or those delivery means that are otherwise effective for delivering the composition of the present invention to the skin, with the resulting rheology of the extruded product preferably falling within the ranges described hereinabove for extruded compositions. Some examples of such perforated caps or other shear force delivery means, and some dispensing packages for use with compositions herein, are described in U.S. Pat. No. 5,000,356, issued to Johnson et al. on Mar. 19, 1991, which description is incorporated herein by reference.

Method of Manufacture

The antiperspirant cream compositions of the present invention may be prepared by any known or otherwise effective technique, suitable for providing an antiperspirant cream composition having the select rheology characteristics described hereinbefore, provided that shear is not applied to the product after its point of solidification. Such methods involve formulation of the essential components of the composition to form a soft cream having the requisite hardness, static yield stress, and delta stress described herein, wherein the crystalline matrix within the soft cream preferably comprises gellant crystals having an average particle diameter that is minimized through methods well known in the formulation art for minimizing crystalline particle size in a composition.

The point of solidification in the manufacturing method herein corresponds to the point at which the composition becomes turbid due to gellant crystallization in the absence of other dispersed solids in the composition, or when the apparent viscosity increases during the solidification process step described herein. In this context, the term "apparent viscosity" means that the viscosity of the composition appears by visual inspection during the solidification step to have increased.

The manufacturing methods preferably result in the formation of crystalline gellant particles having an average particle diameter of less than about 10 $\mu$m, more preferably from about 0.1 $\mu$m to about 5 $\mu$m, even more preferably from about 1 $\mu$m to about 4 $\mu$m. Crystalline particle morphology includes platelets, spheres, needles, and so forth. In this context, the average particle diameter refers to the average particle diameter at about the narrowest section of the crystalline particle.

Crystalline particle size in the preferred embodiments of the present invention can be determined by techniques well known in the art, which include light microscopy of the composition, wherein the composition is formulated for analysis purposes without antiperspirant active or other solid particulates. Without such reformulation, it is more difficult to distinguish crystalline gellant particle size from particle size contributed from other nongellant particulates. The reformulated composition is then evaluated by light microscopy or other similar method.

Methods for preparing the antiperspirant cream compositions of the present invention include those methods well known in the art for formulating compositions containing small gellant crystalline particles. Such methods include the use of nucleating agents, formulation with select carriers or gellants or carrier/gellant combinations, controlling rates of crystallization including controlling formulation and processing temperatures, and so forth. All such methods should be applied to the formulation to control or minimize gellant crystal particle size to form the desired crystalline matrix of the composition and the desired rheology characteristics arising therefrom.

A preferred method for preparing such a composition comprises a formulation step followed by a controlled solidification step. The formulation step involves preparing a flowable liquid comprising 1) from about 5% to about 35% by weight of a particulate antiperspirant active, from about 0.1% to about 20% by weight of a crystalline gellant, and from about 10% to about 80% of an anhydrous liquid carrier for the crystalline gellant, the anhydrous liquid carrier having a solubility parameter of from about 3 to about 13. The process preferably involves thorough mixing together of all of the essential and optional components at the desired temperature while adding minimal amounts of heat or other energy to liquefy and thoroughly mix all of the added ingredients. Processing temperatures will generally range from about 28° C. to about 125° C., more preferably from about 35° C. to about 100° C., even more preferably from about 50° C. to about 90° C., but will vary with the melt profile of the ingredients in the mixture. In this context, the term "liquefy" means that the substantially all of the gellant and carrier material in the composition are melted or are otherwise in the form of a combined flowable liquid, which combined flowable liquid comprises particulate antiperspirant active substantially uniformly dispersed therethrough.

The second essential step in the preferred method of the making the compositions involves solidification of the liquefied mixture described hereinabove. The solidification preferably involves removal of the composition from any added heat or other energy source, and/or by subjecting the liquefied composition to active cooling. It is essential, however, that once the solidification process begins, that the liquefied composition is allowed to solidify to the requisite hardness without the addition of substantial amounts of shear force, preferably without the addition of any additional shear force. It has been found that the addition of such additional shear force during the solidification step results in a crystalline network that is insufficient to maintain the rheology profile described herein. Such additional shear force can break down the desired crystalline network if applied after the point of solidification, and it is the presence of such a structure crystalline network that is largely responsible for the rheology profile described herein, and the product performance and stability benefits resulting therefrom.

The preferred method may further comprise the addition of optional materials to composition. Such addition is preferably during the formulation step, wherein the essential and optional ingredients are mixed together to form a liquefied admixture. In making the compositions of the present invention, care must be taken to assure that the particulate antiperspirant materials are dispersed relatively uniformly throughout the composition.

Method of Use

The antiperspirant cream compositions of the present invention may be packaged in any antiperspirant cream containers known in the art, or other container suitable for topical delivery of a flowable cream to the skin. These packaged compositions may then be applied topically to the skin by any conventional, known or otherwise effective means of topical application. Such methods preferably involve application of an effective amount of the antiperspirant cream composition to the axilla or other area of the skin, preferably from about 0.1 gram to about 20 grams, more preferably from about 0.1 gram to about 10 grams, even more preferably from about 0.1 gram to about 1 gram, of the composition to the desired area of the skin. The applied cream is preferably rubbed over the applied surface using an applicator device or shear force delivery means as described herein, and more preferably such rubbing action is continued until there is little or no visible residue on the applied surface.

These application methods are preferably applied to the desired areas, typically to the axilla or other area of the skin, one to two times daily, preferably once daily, to achieve effective antiperspirant and odor control over an extended period.

A preferred method of using the compositions of the present invention comprises applying the composition topically through an applicator device having a shear force delivery means as described hereinbefore, and which delivers the antiperspirant cream composition of the present invention to the surface of the skin by extrusion through a perforated cap or other shear force delivery means resulting in an extruded antiperspirant cream composition having the delta stress, static yield stress, and penetration force values described hereinbefore for the antiperspirant cream composition after such extrusion.

It has been found that this method of applying shear stress to the composition of the present invention is especially effective in providing even spreading of the composition to the skin, while providing a liquefying shear stress to the composition. The composition quickly shears after extrusion but during topical application to the skin to a creamy liquid that spreads smoothly and uniformly over the skin, and especially over the skin and through axilla hair. The improved spreading results in improved deodorant and antiperspirant efficacy.

The antiperspirant compositions of the present invention may also be used in conventional or otherwise effective manner to treat or prevent perspiration on areas of the human body, such as the axillary areas, which are prone to perspiration wetness. Specifically, an effective amount of any of the compositions described herein is applied topically to such areas one or more times a day. When this is done, the compositions provide effective antiperspirant performance, as well as reduced residue on the skin, and good aesthetics upon application for the user.

EXAMPLES

The following nonlimiting examples illustrate specific embodiments of the antiperspirant cream compositions of the present invention, including methods of manufacture and use.

Each of the exemplified compositions are prepared by combining all of the listed components and heating the combination to 100° C. with agitation to form a hot liquid. The heated liquid is allowed to cool with agitation until just before the point of solidification, at which point the cooled, liquid composition is filled into jars or cream applicators and allowed to cool without further agitation or other applied shear to form a stiff cream within the corresponding applicator package. Each packaged composition is then fitted with the perforated cap as defined in the rheology methodologies described herein, through which the composition may be extruded with shear force and applied topically to the skin.

TABLE I

| Component | Example I | Example II | Example III | Example IV | Example V |
|---|---|---|---|---|---|
| Cyclomethicone D5[1] | 64.0 | 34.5 | 68.5 | 62.25 | 67.25 |
| Al Zr trichlorohydrox glycinate[2] | 26.0 | 26.0 | 26.0 | 26 | 26 |
| Butyl stearate | 5.0 | 34.5 | — | 5.0 | — |
| C20–C40 alcohols[3] | 4.5 | 4.5 | 5.0 | — | — |
| Glyceryl tribehenate | — | — | — | 5.0 | 5.0 |
| C18–C36 triglyceride combination[4] | — | — | — | 1.25 | 1.25 |
| Perfume | 0.5 | 0.5 | 0.5 | 0.5 | 0.5 |
| Rheology | | | | | |
| 1. Hardness (gm force) | 170 | 150 | 200 | 170 | 200 |
| 2. Delta stress (dyne/cm2) | | | | | |
| a) before extrusion | 3,800 | 5,300 | 6,800 | 6,100 | 4,200 |
| b) after extrusion | 3,000 | 3,000 | 7,500 | 7,200 | 3,300 |
| 3. Static yield stress (dyne/cm2) | | | | | |
| a) before extrusion | 16,000 | 4,300 | 2,200 | 11,800 | 30,600 |
| b) after extrusion | 13,200 | 3,000 | 1,600 | 2,600 | 23,000 |

[1]Cyclic polydimethylsiloxane containing 5 carbons, supplied by G. E. Silicones
[2]Supplied by Westwood Chemical Corporation
[3]Unilin 425 Petrolite
[4]Synorowax HGL-C from Croda

TABLE 2

| Component | Example VI | Example VII | Example VIII | Example IX | Example X | Example XII |
|---|---|---|---|---|---|---|
| Cyclomethicone[5] | 34.0 | 62.75 | 62.75 | — | — | 62.75 |
| Dimethicone[6] | — | 5.0 | 5.0 | 5.0 | 69.0 | 5.0 |
| Glyceryl tribehenate | — | — | 5.0 | 5.0 | — | 5.0 |
| C18–36 triglyceride combination[4] | — | — | — | 1.25 | — | — |

TABLE 2-continued

| Component | Example VI | Example VII | Example VIII | Example IX | Example X | Example XII |
|---|---|---|---|---|---|---|
| C20–40 alcohols[3] | — | 1.25 | 1.25 | — | 5.0 | — |
| Hydrogenated rapeseed oil[7] | — | 5.0 | — | — | — | — |
| C20–40 Pareth-3[8] | — | — | — | — | — | 1.25 |
| Diisopropyl adipate | — | — | — | 62.75 | — | — |
| Butyl stearate | 30.0 | — | — | — | — | — |
| Cocamide MEA[9] | 10.0 | — | — | — | — | — |
| Perfume | | | | | | |
| Al Zr trichlorohydrex glycinate[2] | 26.0 | 26.0 | 26.0 | 26.0 | 26.0 | 26.0 |
| Rheology | | | | | | |
| 1. Hardness (gm force) | 218 | 88 | 84 | 117 | 362 | 143 |
| 2. Static yield stress (dyne/cm2) | | | | | | |
| a) before extrusion | 12,700 | 5,300 | 8,300 | 19,550 | 10,200 | 27,200 |
| b) after extrustion | 10,900 | 5,600 | 9,700 | 10,300 | 10,150 | 33,000 |
| 3. Delta stress (dyne/cm2) | | | | | | |
| a) before extrusion | 3,800 | 5,500 | 4,200 | 5,700 | 6,920 | 7,100 |
| b) after extrusion | 2,400 | 4,300 | 2,000 | 3,800 | 5,200 | 6,433 |

[5]Dow Corning 245 Fluid
[6]Dow Corning 200 Fluid 10 Cut viscosity
[7]High Eurcic Acid Hydrogenated Rapeseed Oil from Calgene
[8]Unithox 420 from Petrolite
[9]Coconut monoethanolamide from Mona
[10]Supplied by Westwood Chemical Corporation The exemplified compositions (I–XII) remain physically stable over extended periods of time, exhibit minimal or no solvent syneresis during packaging, storage, transport or even during extrusion through a perforated or mesh cap. The exemplified compositions are also especially effective in spreading uniformly over the skin, especially over hairy areas of the skin, to provide improved antiperspirant and deodorant efficacy.

What is claimed is:

1. An anhydrous antiperspirant cream composition comprising
   (a) from about 5% to about 35% by weight of a particulate antiperspirant active;
   (b) from about 0.1% to about 20% by weight of a crystalline gellant; and
   (c) from about 10% to about 80% by weight of an anhydrous liquid carrier for the crystalline gellant having a solubility parameter of from about 3 to about 13;
wherein the composition is substantially free of polymeric or inorganic thickening agents, and has a penetration force value of from about 75 gram-force to about 500 gram-force, a delta stress value of from about 300 dyne/cm$^2$ to about 8,000 dyne/cm$^2$ as measured after extrusion of the composition through a shear force delivery means, and a static yield stress value of at least about 1,000 dyne/cm$^2$ as measured after extrusion of the composition through a shear force delivery means.

2. The composition of claim 1 wherein the delta stress value is from about 1,000 dyne/cm$^2$ to about 6,000 dyne/cm$^2$ as measured after extrusion of the composition through a shear force delivery means and the static yield stress value is from about 4,000 dyne/cm$^2$ to about 63,000 dyne/cm$^2$ as measured after extrusion of the composition through a shear force delivery means.

3. The composition of claim 2 wherein the delta stress value is from about 1,000 dyne/cm$^2$ to about 5,000 dyne/cm$^2$ as measured after extrusion of the composition through a shear force delivery means and the static yield stress value is from about 4,000 dyne/cm$^2$ to about 35,000 dyne/cm$^2$ as measured after extrusion of the composition through a shear force delivery means.

4. The composition of claim 3 wherein the composition contains less than 1% by weight of polymeric thickening agent, inorganic thickening agent, or combinations thereof.

5. The composition of claim 4 wherein the composition contains zero percent by weight of polymeric thickening agent, inorganic thickening agent, or combinations thereof.

6. The composition of claim 2 wherein the penetration force value is from about 100 gram-force to about 400 gram-force.

7. The composition of claim 1 wherein said composition has a static stress value of at least about 4,000 dyne/cm$^2$ as measured prior to extrusion through a shear force delivery means, and a delta stress value of from about 300 dyne/cm$^2$ to about 8,000 dyne/cm$^2$ as measured prior to extrusion of the composition through a shear force delivery means.

8. The composition of claim 7 wherein the penetration force value is from about 100 gram-force to about 400 gram-force.

9. The composition of claim 1 wherein the crystalline gellant is selected from the group consisting of coconut monoethanolamide, glyceryl tribehenate, C18 to C36 triglycerides, hydrogenated rapeseed oil, fatty alcohols having from about 20 to about 40 carbon atoms, C20 to C40 pareth-3, and combinations thereof.

10. The composition of claim 9 wherein the composition comprises from about 5% to about 20% of coconut monoethanolamide by weight of the composition.

11. The composition of claim 10 wherein the composition comprises a volatile silicone carrier.

12. The composition of claim 9 wherein the composition comprises a first gellant selected from the group consisting of a fatty alcohol having from about 20 to about 40 carbon atoms, C20 to C40 pareth-3, and combinations thereof, and a second gellant selected from the group consisting of glyceryl tribehenate, hydrogenated rapeseed oil, and combinations thereof, wherein the weight ratio of the first gellant to the second gellant is from about 1:20 to about 1:1.

13. The composition of claim 12 wherein the composition comprises a volatile silicone carrier, and wherein the weight ratio of the first gellant to the second gellant is from about 1:10 to about 1:3.

14. The composition of claim 13 wherein the composition comprises a volatile silicone carrier.

15. A packaged anhydrous antiperspirant cream composition, comprising
   (c) from about 5% to about 35% by weight of a particulate antiperspirant active;
   (b) from about 0.1% to about 20% by weight of a crystalline gellant; and
   (c) from about 10% to about 80% by weight of an anhydrous liquid carrier for the crystalline gellant material, the anhydrous liquid carrier having a solubility parameter of from about 3 to about 13;
   (d) a delivery means suitable for application of shear force to the composition during delivery from the packaged composition through the delivery means;
wherein the composition is substantially free of polymeric or inorganic thickening agents, and has a penetration force value of from about 75 gram-force to about 500 gram-force, a delta stress value of from about 300 dyne/cm$^2$ to about 8,000 dyne/cm$^2$ as measured after extrusion of the composition through a shear force delivery means, and a static yield stress value of at least about 1,000 dyne/cm$^2$ as measured after extrusion of the composition through a shear force delivery means.

16. The packaged composition of claim 15 wherein the shear force delivery means is a rounded convex surface having a plurality of apertures through which the composition is extruded prior to application to the skin, wherein the rounded convex surface has a radius of curvature of from about 25 mm to about 127 mm for a major dimension; a radius of curvature of from about 12 mm to about 39 mm for a minor dimension; an average aperture diameter of from about 1.9 mm to about 2.6 mm; average aperture spacing of from about 0.25 mm to about 13 mm; a surface thickness of from about 0.25 mm to about 1.53 mm; a dome major axis of from about 38 mm to about 77 mm; and a dome minor axis of from about 12 mm to about 51 mm.

17. The packaged composition of claim 16 wherein the delta stress value is from about 1,000 dyne/cm$^2$ to about 6,000 dyne/cm$^2$ as measured after extrusion of the composition through a shear force delivery means and the static yield stress value is from about 4,000 dyne/cm$^2$ to about 63,000 dyne/cm$^2$ as measured after extrusion of the composition through a shear force delivery means.

18. The packaged composition of claim 17 wherein the delta stress value is from about 1,000 dyne/cm$^2$ to about 5,000 dyne/cm$^2$ as measured after extrusion of the composition through a shear force delivery means and the static yield stress value is from about 4,000 dyne/cm$^2$ to about 35,000 dyne/cm$^2$ as measured after extrusion of the composition through a shear force delivery means.

19. The packaged composition of claim 18 wherein the composition contains less than about 1% by weight of polymeric thickening agent, inorganic thickening agent, or combinations thereof.

20. The packaged composition of claim 19 wherein the composition contains zero percent by weight of polymeric thickening agent, inorganic thickening agent, or combinations thereof.

21. The packaged composition of claim 18 wherein the penetration force value is from about 100 gram-force to about 400 gram-force.

22. The packaged composition of claim 15 wherein said composition has a static yield stress value of at least about 4,000 dyne/cm$^2$ as measured prior to extrusion through a shear force delivery means, and a delta stress value of from about 300 dyne/cm$^2$ to about 8,000 dyne/cm$^2$ as measured prior to extrusion of the composition through a shear force delivery means.

23. The composition of claim 22 wherein the penetration force value is from about 100 gram-force to about 400 gram-force.

24. A method of making an improved anhydrous antiperspirant cream composition, which method comprises the steps of:
   (a) preparing a flowable liquid comprising:
      (i) from about 5% to about 35% by weight of a particulate antiperspirant active;
      (ii) from about 0.1% to about 20% by weight of a crystalline gellant; and
      (iii) from about 10% to about 80% by weight of an anhydrous liquid carrier for the crystalline gellant material, the anhydrous liquid carrier having a solubility parameter of from about 3 to about 13;
   (b) solidifying the flowable liquid, without application of shear force to the composition after the point of solidification of the composition, wherein the solidified composition is substantially free of polymeric or inorganic thickening agents, and wherein the composition has a penetration force value of from about 75 gram-force to about 500 gram-force, a delta stress value of from about 300 dyne/cm$^2$ to about 8,000 dyne/cm$^2$ as measured after extrusion of the composition through a shear force delivery means, and a static yield stress value of at least about 1,000 dyne/cm$^2$ as measured after extrusion of the composition through a shear force delivery means.

25. The method of claim 24 wherein the delta stress value is from about 1,000 dyne/cm$^2$ to about 6,000 dyne/cm$^2$ as measured after extrusion of the composition through a shear force delivery means and the static yield stress value is from about 4,000 dyne/cm$^2$ to about 63,000 dyne/cm$^2$ as measured after extrusion of the composition through a shear force delivery means.

26. The composition of claim 25 wherein the delta stress value is from about 1,000 dyne/cm$^2$ to about 5,000 dyne/cm$^2$ as measured after extrusion of the composition through a shear force delivery means and the static yield stress value is from about 4,000 dyne/cm$^2$ to about 35,000 dyne/cm$^2$ as measured after extrusion of the composition through a shear force delivery means.

27. The composition of claim 26 wherein the composition contains less than 1% by weight of polymeric thickening agent, inorganic thickening agent, or combinations thereof.

28. The composition of claim 27 wherein the composition contains zero percent by weight of polymeric thickening agent, inorganic thickening agent, or combinations thereof.

29. The composition of claim 26 wherein the penetration force value is from about 100 gram-force to about 400 gram-force.

30. The composition of claim 24 wherein said composition has a static yield stress value of at least about 4,000 dyne/cm$^2$ as measured prior to extrusion through a shear force delivery means, and a delta stress value of from about 300 dyne/cm$^2$ to about 8,000 dyne/cm$^2$ as measured prior to extrusion of the composition through a shear force delivery means.

31. The method of claim 30 wherein the penetration force value is from about 100 gram-force to about 400 gram-force.

32. An anhydrous antiperspirant cream composition comprising
(a) from about 5% to about 35% by weight of a particulate antiperspirant active;
(b) from about 0.1% to about 20% by weight of a crystalline gellant; and
(c) from about 10% to about 80% by weight of an anhydrous liquid carrier for the crystalline gellant having a solubility parameter of from about 3 to about 13;
wherein the composition is substantially free of polymeric or inorganic thickening agents, and has a penetration force value of from about 75 gram-force to about 500 gram-force, a delta stress value of from about 300 dyne/cm$^2$ to about 8,000 dyne/cm$^2$ as measured prior to extrusion of the composition through a shear force delivery means, and a static yield stress value of at least about 1,000 dyne/cm$^2$ as measured prior to extrusion of the composition through a shear force delivery means.

33. The composition of claim 32 wherein the delta stress value is from about 1,000 dyne/cm$^2$ to about 6,000 dyne/cm$^2$ and the static yield stress value is from about 4,000 dyne/cm$^2$ to about 63,000 dyne/cm$^2$.

34. The composition of claim 33 wherein the delta stress value is from about 1,000 dyne/cm$^2$ to about 5,000 dyne/cm$^2$ and the static yield stress value is from about 8,000 dyne/cm$^2$ to about 63,000 dyne/cm$^2$.

35. The composition of claim 33 wherein the composition contains less than 1% by weight of polymeric thickening agent, inorganic thickening agent, or combinations thereof.

36. The composition of claim 35 wherein the composition contains zero percent by weight of polymeric thickening agent, inorganic thickening agent, or combinations thereof.

37. The composition of claim 33 wherein the penetration force value is from about 100 gram-force to about 400 gram-force.

38. The composition of claim 32 wherein the crystalline gellant is selected from the group consisting of coconut monoethanolamide, glyceryl tribehenate, C18 to C36 triglycerides, hydrogenated rapeseed oil, fatty alcohols having from about 20 to about 40 carbon atoms, C20 to C40 pareth-3, and combinations thereof.

39. The composition of claim 38 wherein the composition comprises from about 5% to about 20% of coconut monoethanolamide by weight of the composition.

40. The composition of claim 38 wherein the composition comprises a volatile silicone carrier.

41. The composition of claim 38 wherein the composition comprises a first gellant selected from the group consisting of a fatty alcohol having from about 20 to about 40 carbon atoms, C20 to C40 pareth-3, and combinations thereof, and a second gellant selected from the group consisting of glyceryl tribehenate, hydrogenated rapeseed oil, and combinations thereof, wherein the weight ratio of the first gellant to the second gellant is from about 1:20 to about 1:1.

42. The composition of claim 41 wherein the composition comprises a volatile silicone carrier, and wherein the weight ratio of the first gellant to the second gellant is from about 1:10 to about 1:3.

43. The composition of claim 13 wherein the composition comprises a volatile silicone carrier.

44. A method for treating and preventing perspiration in humans, which method comprises the applying from about 0.1 gram to about 20 grams of the composition of claim 1 to the skin.

45. A method for treating and preventing perspiration in humans, which method comprises the applying from about 0.1 gram to about 20 grams of the packaged composition of claim 15 to the skin.

46. A method for treating and preventing perspiration in humans, which method comprises the applying from about 0.1 gram to about 20 grams of the composition of claim 24 to the skin.

47. A method for treating and preventing perspiration in humans, which method comprises the applying from about 0.1 gram to about 20 grams of the composition of claim 32 to the skin.

* * * * *